United States Patent [19]

Roth et al.

[11] Patent Number: 5,274,154

[45] Date of Patent: Dec. 28, 1993

[54] STABILIZATION OF ORGANOSILOXANES CONTAINING SIOC-BONDED RADICALS

[75] Inventors: Michael Roth; Günter von Au, both of Burghausen; Christa Blümlhuber, Neuötting; Richard Weidner; Edgar Schmidt, both of Burghausen; Christian Solbrig, Mehring, all of Fed. Rep. of Germany

[73] Assignee: Wacker-Chemie GmbH, Munich

[21] Appl. No.: 79,789

[22] Filed: Jun. 23, 1993

[30] Foreign Application Priority Data

Jul. 16, 1992 [DE] Fed. Rep. of Germany ....... 4223468

[51] Int. Cl.⁵ .......................... C07F 7/08; C07F 7/18
[52] U.S. Cl. .................................................. 556/401
[58] Field of Search ........................................ 556/401

[56] References Cited

U.S. PATENT DOCUMENTS 2,990,419  6/1961  Nitzsche et al. ............... 556/401
4,732,994  3/1988  Riederer et al. ............... 556/401
5,034,446  7/1991  Kendall et al. ................ 556/401 X

*Primary Examiner*—Paul F. Shaver

[57] ABSTRACT

A process for stabilizing organosiloxanes containing SiOC-bonded radicals, by treating the organosiloxanes with compounds which scavenge hydroxyl groups, selected from (a) organic isocyanates, (b) compounds of the general formula $$X_mSiR_n \qquad (I)$$

in which X represents a radical of the general formula $$R^1COO- \qquad (II)$$

or a radical of the general formula $$RR^1C=N-O- \qquad (III)$$

where R represents an optionally halogen-substituted $C_1$ to $C_{16}$-hydrocarbon radical, $R^1$ is the same as R or a hydrogen atom, m is 1, 2, 3 or 4, n is 0, 1, 2 or 3 and the sum of $m+n=4$, and mixtures thereof.

6 Claims, No Drawings

STABILIZATION OF ORGANOSILOXANES CONTAINING SIOC-BONDED RADICALS

The invention relates to stabilized organosiloxanes containing SiOC-bonded radicals, and more particularly to a process for stabilizing organosiloxanes by treating the organosiloxanes with compounds which scavenge hydroxyl groups.

BACKGROUND OF THE INVENTION

Organosiloxanes containing SiOC-bonded radicals, such as alkoxysiloxanes, tend to equilibrate on storage, in particular in the presence of a catalyst. In this process, easily volatile compounds are formed which greatly reduce the flash point of the product. A low flash point is undesired when the product is used, for example, for the treatment of construction materials.

European Patent A-249,960 describes a process for stabilizing organopolysiloxane oils containing SiC-bonded hydrocarbon radicals, in which hexamethyldisilazane, N,N-bistrimethylsilylacetamide (BSA) and N,N'-bistrimethylsilylurea are employed as stabilizers. These oils form fewer degradation products on thermal and mechanical stress. The above compounds are not suitable for stabilizing organosiloxanes containing SiOC-bonded radicals, since they show no, or only a slight stabilizing effect.

Therefore, it is an object of the present invention to stabilize organosiloxanes containing SiOC-bonded radicals such that the formation of easily volatile compounds on storage is suppressed, even in the presence of a catalyst. A further object of the present invention is to increase the flash point of organosiloxanes containing SiOC-bonded radicals by addition of a stabilizer.

SUMMARY OF THE INVENTION

The foregoing objects and others which will become apparent from the following description are accomplished in accordance with this invention generally speaking, by providing a process for stabilizing organosiloxanes containing SiOC-bonded radicals, in which the organosiloxanes are treated with compounds which scavenge hydroxyl groups, which are selected from (a) organic isocyanates, (b) compounds of the general formula $$X_m SiR_n. \qquad (I)$$

in which X represents a radical of the general formula $$R^1 COO— \qquad (II)$$

or of the general formula $$RR^1 C=N—O— \qquad (III)$$

where R represents a $C_1$ to $C_{16}$-hydrocarbon radical or a halogen-substituted $C_1$ to $C_{16}$-hydrocarbon radical and $R^1$ is the same as R or a hydrogen atom, m is 1, 2, 3 or 4, n is 0, 1, 2 or 3 and the sum of m+n=4, or mixtures thereof.

DESCRIPTION OF THE INVENTION

Suitable organic isocyanates which scavenge hydroxyl groups are all the known organic isocyanates. Examples of suitable organic isocyanates are mono-, di- and polyisocyanates, such as 4-tolysulfonyl isocyanate, 2,6- and 3,5-dichlorophenyl isocyanate, 2,6-diisopropylphenyl isocyanate, 3-isocyanatomethyl-3,5,5-trimethylcyclohexyl isocyanate and its polymers, polyisocyanates based on diphenylmethane diisocyanate, polymers of diphenylmethane diisocyanate, polymers of hexamethylene-1,6-diisocyanate, trimethylsilyl isocyanate, and reaction products, containing isocyanate groups, of di- or polyisocyanates with organic or organosilicon compounds having terminal hydroxyl groups. Polyisocyanates are preferably used in the process of this invention because of their low volatility and 3-isocyanatomethyl-3,5,5-trimethylcyclohexyl isocyanate (isophorone diisocyanate) is particularly preferred.

The compounds which scavenge hydroxyl groups, which have the general formula (I) in which X represents a radical of general formula (II), are described, for example, in W. Noll, 2nd edition 1968, Verlag Chemie, Weinheim, chap. 3.10. The radical $R^1$ in general formula (II) preferably represents a methyl radical, R represents a $C_1$ to $C_6$-alkyl radical and m is a value of 2 or 3. Ethyltriacetoxysilane is particularly preferred.

The compounds which scavenge hydroxyl groups, which have the general formula (I) in which X represents a radical of general formula (III), are described, for example, in "Mechanismus und Strukturen in der organischen Chemie" (Mechanism and structures in organic chemistry), Edwin S. Gould, Verlag Chemie, Weinheim, 1969, page 748. The radical $R^1$ in general formula (III) preferably represents a hydrogen atom or a $C_1$ to $C_6$-alkyl radical, and in particular a $C_1$ to $C_6$-alkyl radical, R represents a $C_1$ to $C_6$-alkyl radical and m is a value of 3 or 4. Methyl-tris(methylethylketoximo)silane, tetra(methylethylketoximo)silane and vinyl-tris(methylethylketoximo)silane are particularly preferred.

Examples of the $C_1$ to $C_{16}$-hydrocarbon radicals represented by R are alkyl radicals, such as the methyl, ethyl, n-propyl, isopropyl, n-butyl, isobutyl, tert-butyl, n-pentyl, isopentyl, neopentyl or tert-pentyl radicals; hexyl radicals, such as the n-hexyl radical; heptyl radicals, such as the n-heptyl radical; octyl radicals, such as the n-octyl radical and isooctyl radicals, such as the 2,2,4-trimethylpentyl radical; nonyl radicals, such as the n-nonyl radical; decyl radicals, such as the n-decyl radical; dodecyl radicals, such as the n-dodecyl radical; alkenyl radicals, such as the vinyl and the allyl radicals; cycloalkyl radicals, such as cyclopentyl, cyclohexyl or cycloheptyl radicals and methylcyclohexyl radicals; aryl radicals, such as the phenyl, naphthyl, anthryl and phenanthryl radicals; alkaryl radicals, such as o-, m- or p-tolyl radicals; xylyl radicals and ethylphenyl radicals; aralkyl radicals, such as the benzyl radical, and the α-, β-phenylethyl radicals.

Examples of halogen-substituted $C_1$ to $C_{16}$-hydrocarbon radicals represented by R are alkyl radicals substituted by fluorine, chlorine, bromine and iodine atoms, such as the 3,3,3-trifluoro-n-propyl radical, the 2,2,2,2',2',2'-hexafluoroisopropyl radical, the heptafluoroisopropyl radicals, and haloaryl radicals, such as the o-, m- and p-chlorophenyl radicals.

The process of this invention may be used for stabilizing all organosiloxanes containing SiOC-bonded radicals, independently of their molecular weight and their structure, i.e., linear and branched low molecular weight organosiloxanes and polyorganosiloxanes.

Organosiloxanes of the general formula $$R_xSi(OR^2)_y(OH)_zO_{\frac{4-x-y-z}{2}} \quad (IV)$$

can be effectively stabilized, where R is the same as above, $R^2$ represents a $C_1$ to $C_6$-alkyl radical, x is 0, 1, 2 or 3, with an average of from 0.9 to 1.8, y is 0, 1, 2 or 3, with an average of from 0.5 to 1.5, z is 0, 1, 2 or 3, with an average of from 0.0 to 0.5, and the sum of x+y+z is at most 3.5. Organosiloxanes of this type can be prepared, for example, by the process described in U.S. Pat. No. 4,209,454.

The process of this invention is particularly suitable for stabilizing organopolysiloxanes treated with condensation catalysts, such as, for example, those used in the treatment of construction materials.

The condensation catalysts can be acidic, neutral or basic. Examples of such condensation catalysts are, in particular, carboxylic acid salts of tin or zinc, it being possible for hydrocarbon radicals to be bonded directly to tin, such as di-n-butyltin dilaurate, tin octoates, di-2-ethyltin dilaurate, di-n-butyltin di-2-ethylhexoate, di-2-ethylhexyltin di-2-ethylhexoate, dibutyl- or dioctyltin diacylates, in which the acylate groups are derived from alkanoic acids having from 3 to 16 carbon atoms per acid, in which at least two of the valencies of the carbon atom bonded to the carboxyl group are saturated by at least two other carbon atoms than that of the carboxyl group, and zinc octoates. Additional examples of catalysts are alkoxytitanates, such as butyl titanates and triethanolamine titanate, as well as zirconium and aluminum compounds, especially carboxylic acid salts and alkoxides thereof.

The stabilizer compounds employed to scavenge hydroxyl groups are selected such that no reaction of the stabilizer with the condensation catalyst takes place. For example, an organic isocyanate is not employed as a stabilizer for organosiloxanes which are treated with amines or alcohols.

The process of this invention is also suitable for organosiloxanes containing SiOC-bonded radicals which in addition to catalysts optionally contain silanes of the general formula $$(RO)_mSiR_n. \quad (V)$$

where R, m, n and the sum of m+n are the same as above. The radical R in general formula (V) preferably represents a $C_1$ to $C_6$-alkyl radical and m is a value of 3 or 4. The organosiloxanes containing SiOC-bonded radicals preferably contain at most 90% by weight, and in particular up to about 50% by weight, of silanes of general formula (V).

In the process of this invention, the organosilanes are preferably treated with from 0.01 to 5% by weight, and in particular from 0.25 to 3% by weight of the compounds which scavenge hydroxyl groups. The compound which scavenge hydroxyl groups are preferably added to the organosiloxane cold.

In the following examples, unless otherwise specified, (a) all quantitative data is by weight; (b) all pressures are 0.10 MPa (abs.); and (c) all temperatures are 25° C.

EXAMPLE 1

An organosiloxane (A) prepared by the continuous process described in U.S. Pat. No. 4,209,454, where methyltrichlorosilane, isooctyltrichlorosilane, methanol and water in a weight ratio such as 75:25:32:16 were employed as raw material, with a viscosity of 14.3 mm²/s was treated with 1.0% by weight of dibutyltin laurate and various amounts of isophorone diisocyanate (IPDI). The flash point immediately after the preparation of the mixtures (initial) and after storage for 3 weeks at +50° C. was tested. The measured values are shown in Table 1.

TABLE II

| Flash points according to DIN 51758* | Initial | After 3 weeks/ +50° C. |
|---|---|---|
| Without ethyltriacetoxysilane | 48/49° C. | 40/40° C. |
| 0.5% by weight ethyltriacetoxysilane | 64/63° C. | 52/54° C. |
| 1.0% by weight ethyltriacetoxysilane | 74/74° C. | 57/60° C. |
| 2.0% by weight ethyltriacetoxysilane | 79/83° C. | 62/65° C. |

*measured with two different production batches of the organosiloxane (A).

EXAMPLE 2

An organopolysiloxane (A), prepared in accordance with the procedure described in Example 1, to which 1.0 part by weight of dibutyltin dilaurate had been added, was treated with various amounts of ethyltriacetoxysilane. The flash point of these mixtures was measured immediately after preparation (initial) and after storage for 3 weeks at +50° C. The values are shown in Table II.

TABLE II

| Flash points according to DIN 51758* | Initial | After 3 weeks/ +50° C. |
|---|---|---|
| Without ethyltriacetoxysilane | 48/49° C. | 40/40° C. |
| 0.5% by weight ethyltriacetoxysilane | 64/63° C. | 52/54° C. |
| 1.0% by weight ethyltriacetoxysilane | 74/74° C. | 57/60° C. |
| 2.0% by weight ethyltriacetoxysilane | 79/83° C. | 62/65° C. |

*measured with two different production batches of the organosiloxane (A).

EXAMPLE 3

(a) Organosiloxane (A)
(b) Organosiloxane consisting of a mixture of organosiloxane (A), organosiloxane (B), prepared by the continuous process described in U.S. Pat. No. 4,209,454, in which the raw materials methyltrichlorosilane, ethanol and water were employed in a weight ratio of 152:40:20, with a viscosity of 25 mm²/s; isooctyltriethoxysilane and ethyl silicate with a viscosity of 4.0 mm²/s in a weight ratio of 30:30:19:20.
(c) Mixture of organosiloxane (A) and a highly disperse silicic acid having a specific surface area of 300 m²/g in a weight ratio of 99:1. 1.0 part by weight of dibutyltin dilaurate and various amounts of ethyltriacetoxysilane were in each case added to the products (a), (b) and (c).

The flash point was measured within 24 hrs. after the preparation of the mixtures and after storage for 2 weeks at 50° C. The values are shown in Table III.

TABLE III

| Flash points according to DIN 51758 | Initial | After 2 weeks/ +50° C. |
|---|---|---|
| Organosiloxane (a) without ethyltriacetoxysilane | 50° C. | 39° C. |
| Organosiloxane (a) with | | |
| 0.5% by weight of ethyltriacetoxysilane | 67° C. | 57° C. |
| 1.0% by weight of ethyltriacetoxysilane | 81° C. | 58° C. |
| 1.5% by weight of ethyltriacetoxysilane | 90° C. | 68° C. |
| Organosiloxane (b) without ethyltriacetoxysilane | 49° C. | 51° C. |
| Organosiloxane (b) with | | |
| 0.5% by weight of ethyltriacetoxysilane | 60° C. | 47° C. |

TABLE III-continued

| Flash points according to DIN 51758 | Initial | After 2 weeks/ +50° C. |
|---|---|---|
| 1.0% by weight of ethyltriacetoxysilane | 71° C. | 46° C. |
| 1.5% by weight of ethyltriacetoxysilane | 80° C. | 62° C. |
| Organosiloxane (c) without ethyltriacetoxysilane | 52° C. | 36° C. |
| Organosiloxane (c) with | | |
| 0.5% by weight of ethyltriacetoxysilane | 71° C. | 51° C. |
| 1.0% by weight of ethyltriacetoxysilane | 80° C. | 61° C. |
| 1.5% by weight of ethyltriacetoxysilane | 93° C. | 75° C. |

EXAMPLE 4

Mixtures containing 96.0 parts by weight of the organosiloxane (A) described in Example 1, 1.0 part by weight of dibutyltin dilaurate and 3.0 parts by weight of the oximosilanes described in Table IV were investigated for their flash point immediately after preparation and after storage for 2 weeks at +50° C.

M represents methyl-tris(methylethylketoximo)silane
T represents tetra(methylethylketoximo)silane
V represents vinyl-tris(methylethylketoximo)silane

TABLE IV

| Flash points according to DIN 51758* | Initial | After 2 weeks/ at +50° C. |
|---|---|---|
| Oximosilane | | |
| (a) without addition* | 55° C. | 37° C. |
| (b) M:T 88:12** | 83° C. | 50° C. |
| (c) M:T 91.9:8.1** | 77° C. | 50° C. |
| (d) M | 70° C. | 50° C. |
| (e) V | 85° C. | 49° C. |

*Only 99.0 parts by weight of organosiloxane (A) and 1.0 part by weight of dibutyltin dilaurate
**Mixtures of the two ketoximes in the quantitative ratio indicated

COMPARISON EXAMPLE V₁

An organopolysiloxane (A), prepared in accordance with Example 1, to which 1.0% by weight of dibutyltin dilaurate had been added, was treated with various compounds which scavenge hydroxyl groups. The flash point of these mixtures were measured immediately after preparation (initial) and after storage for 2 weeks at +50° C. The values are shown in Table V.

TABLE V

| | Initial | After 2 weeks/ +50° C. |
|---|---|---|
| (Untreated) | | |
| Flash point-DIN 51758 | 49° C. | |
| Flash point-DIN 51755 | | 40° C. |

TABLE V-continued

| | Initial | After 2 weeks/ +50° C. |
|---|---|---|
| 1% Hexamethyldisilazane (Precipitated after 24 hr at room temperature) | | |
| 1% Silylamine | | |
| Flash point-DIN 51755 | 34° C. | |
| Flash point-DIN 51755 | | 33° C. |
| 1% N,N-bistrimethylsilylacetamide (Precipitated after 24 hr at room temperature) | | |
| 1% Ethyltriacetoxysilane | | |
| Flash point-DIN 51758 | 78° C. | |
| Flash point-DIN 51758 | | 65° C. |

What is claimed is:

1. A process for stabilizing organosiloxanes containing SiOC-bonded radicals, which comprises treating the organosiloxanes with a compound which are scavenges for hydroxyl groups, in which the scavenges are selected from the group consisting of (a) organic isocyanates and (b) compounds of the general formula $$X_mSiR_n,\qquad\text{(I)}$$

in which X is a radical of the general formula $$R^1COO-\qquad\text{(II)}$$

or a radical of the general formula $$RR^1C=N-O-\qquad\text{(III)}$$

where R is a $C_1$ to $C_{16}$-hydrocarbon radical or a halogen-substituted $C_1$ to $C_{16}$-hydrocarbon radical, $R^1$ is the same as R or a hydrogen atom, m is 1, 2, 3 or 4, n is 0, 1, 2 or 3 and the sum of m+n=4, and mixtures thereof.

2. The process of claim 1, wherein the organosiloxanes are organopolysiloxanes containing a condensation catalyst.

3. The process of claim 1, wherein the compound is isophorone diisocyanate.

4. The process of claim 1, where the compound has the general formula (I), in which X represents a radical of general formula (II), $R^1$ represents a methyl radical, R represents a $C_1$ to $C_6$-alkyl radical and m is 2 or 3.

5. The process of claim 1, wherein the compound has the general formula (I), in which X represents a radical of the general formula (III), $R^1$ represents a hydrogen atom or a $C_1$ to $C_6$-alkyl radical, R represents a $C_1$ to $C_6$-alkyl radical and m is 3 or 4.

6. The process of claim 1, wherein the organosiloxanes are treated with from 0.01 to 5% by weight of the scavenger compound for hydroxyl groups.

* * * * *